US00PP27058P3

(12) United States Plant Patent
Evers

(10) Patent No.: US PP27,058 P3
(45) Date of Patent: Aug. 16, 2016

(54) CLIMBING ROSE PLANT NAMED 'TAN07877'

(50) Latin Name: ***Rosa* L**
Varietal Denomination: Tan07877

(71) Applicant: Rosen Tantau KG, Uetersen (DE)

(72) Inventor: Christian Evers, Uetersen (DE)

(73) Assignee: Rosen Tantau KG, Uetersen (DE)

( * ) Notice: Subject to any disclaimer, the term of this patent is extended or adjusted under 35 U.S.C. 154(b) by 79 days.

(21) Appl. No.: 14/544,008

(22) Filed: Nov. 12, 2014

(65) Prior Publication Data

US 2016/0135339 P1 May 12, 2016

(51) Int. Cl.
*A01H 5/02* (2006.01)

(52) U.S. Cl.
USPC ..... Plt./112

(58) Field of Classification Search
USPC ..... Plt./112
See application file for complete search history.

(56) References Cited

PUBLICATIONS

UPOV hit on climbing rose denominated 'TAN07877', QZ PBR 40088, published Aug. 16, 2013.*

* cited by examiner

*Primary Examiner* — Anne Grunberg
(74) *Attorney, Agent, or Firm* — Klarquist Sparkman, LLP

(57) ABSTRACT

A relatively tall mini-climbing rose plant is disclosed that has many branches and many double flowers, many small umbels, flowers that are a yellow-orange color and flowers that lack fragrance.

7 Drawing Sheets

Genus and species: *Rosa* L.
Variety denomination: 'Tan07877'.

ORIGIN OF THE INVENTION

The present invention relates to a new and distinct variety of a climbing rose plant named 'Tan07877' which was originated by me by crossing the variety 'Top Marks' (seed parent, unpatented), with the variety 'Gebrüder Grimm' (pollen parent, unpatented).

BACKGROUND OF THE INVENTION

The primary objective of this breeding was to produce a new climbing rose variety.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. A relatively tall mini-climbing rose plant.
2. A climbing rose plant that produces many branches and many double flowers.
3. A climbing rose plant with yellow-orange flowers.
4. Flowers that lack fragrance.
5. A climbing rose plant with many small umbels.

Asexual reproduction of this new variety by cuttings and budding, as performed at Uetersen, Germany, shows that the foregoing and all other characteristics and distinctions come true to form and are established and transmitted through succeeding propagations. First asexual propagation of this new variety was performed in 2006.

COMPARISON WITH PARENTS

Compared to its female parent, 'Top Marks', which typically grows to 30 to 40 cm, 'Tan07877' grows higher (150 to 200 cm). Compared to its female parent which has an orange-red flower color, 'Tan07877' has a yellow-orange flower color. Compared to its female parent, the flower shape of 'Tan07877' is strong double, the female parent's flower shape is similar. Compared to its male parent, 'Gebrüder Grimm', which typically grows to 60 to 70 cm, 'Tan07877' grows higher (150 to 200 cm).

COMPARISON WITH SIMILAR VARIETY

Compared to a similar variety, 'Tan06225' (Pending U.S. Plant patent application Ser. No. 14/121,999), which has a flower color of violet, turning to light blue, 'Tan07877' has a yellow-orange flower color.

BRIEF DESCRIPTION OF THE ILLUSTRATIONS

The accompanying illustrations of FIGS. 1-7 show typical specimens of the vegetative growth and flowers of this new variety in different stages of development, depicted in color as nearly true as it is reasonably possible to make the same in a color illustration of this character; wherein.

DETAILED BOTANICAL DESCRIPTION

Figure 1:
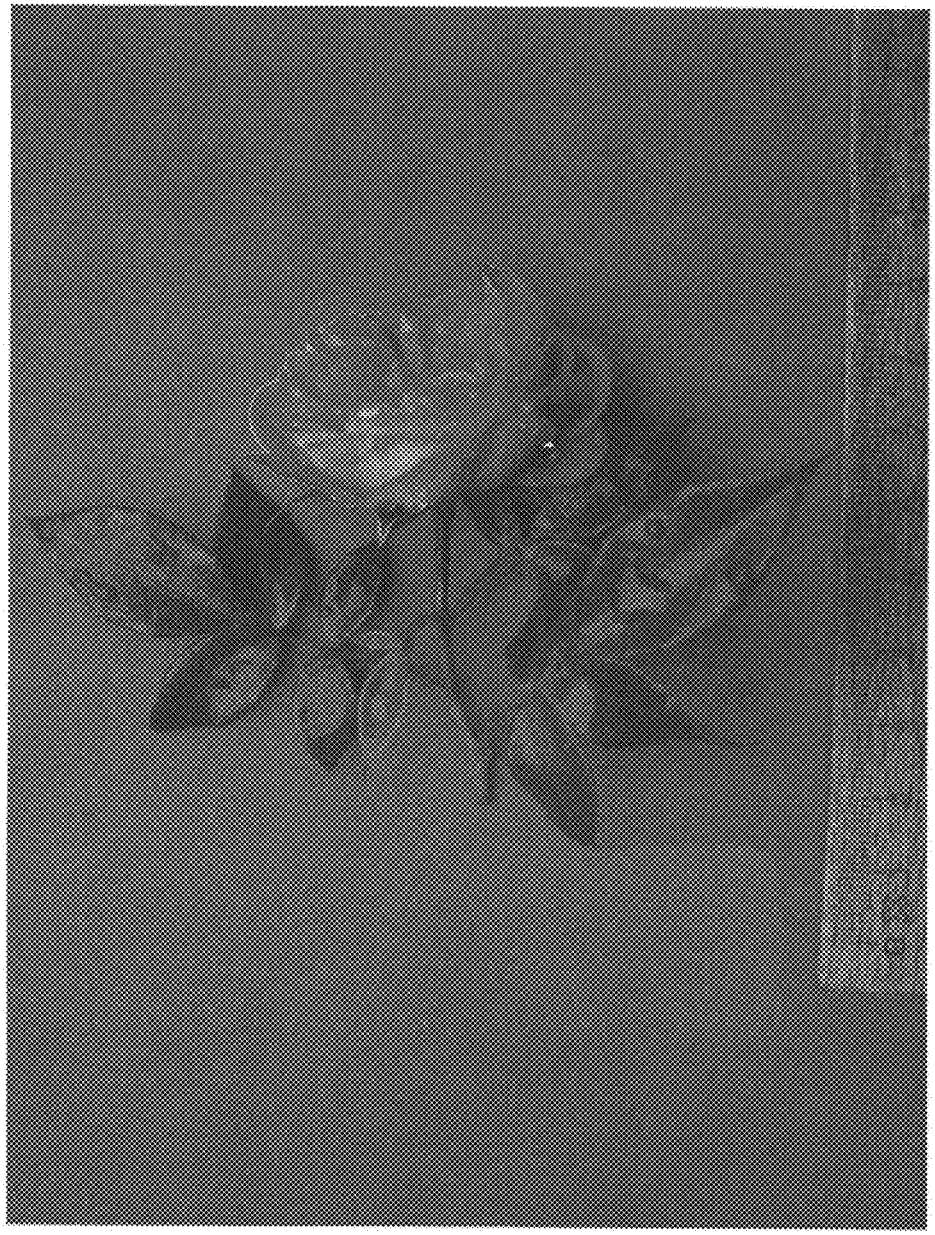
FIG. 1 is a photograph of a branch, foliage and a flower of the new variety.
Figure 2:
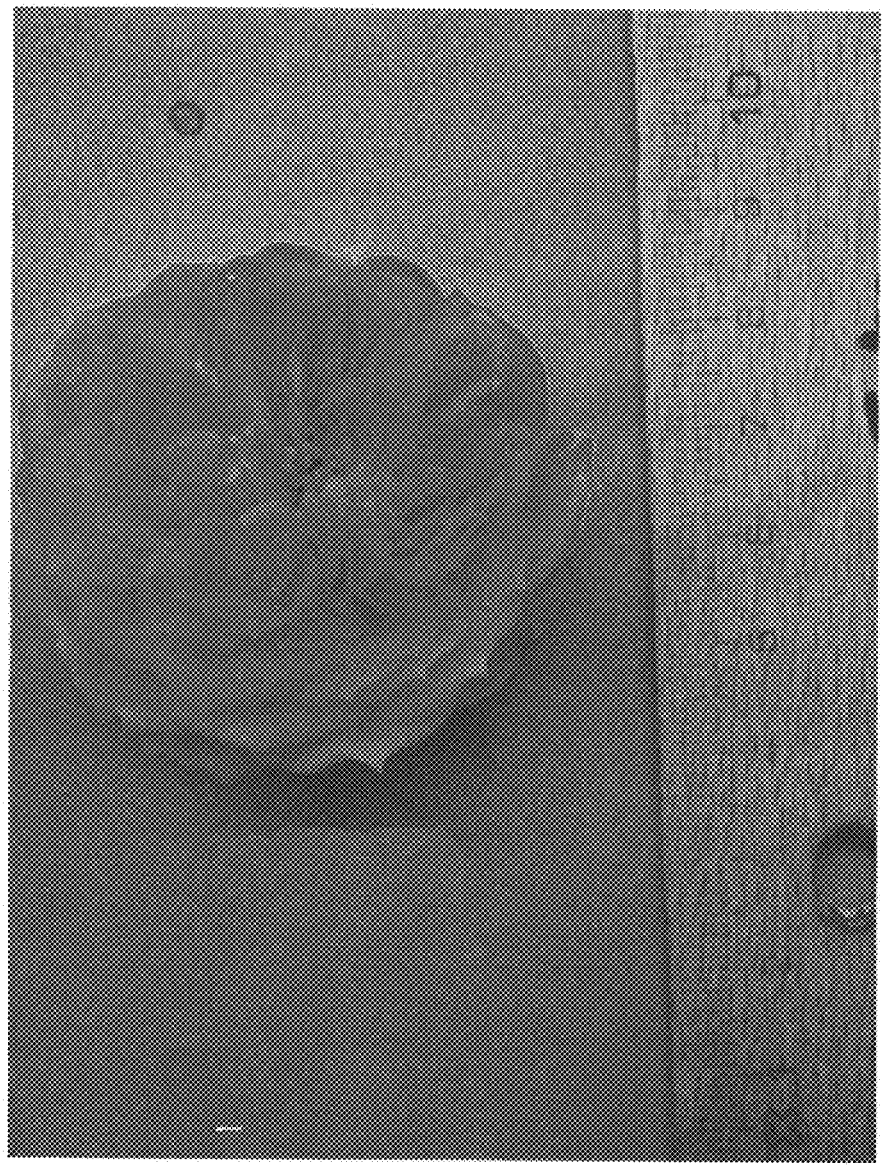
FIG. 2 is a photograph of an open flower of the new variety.
Figure 3:
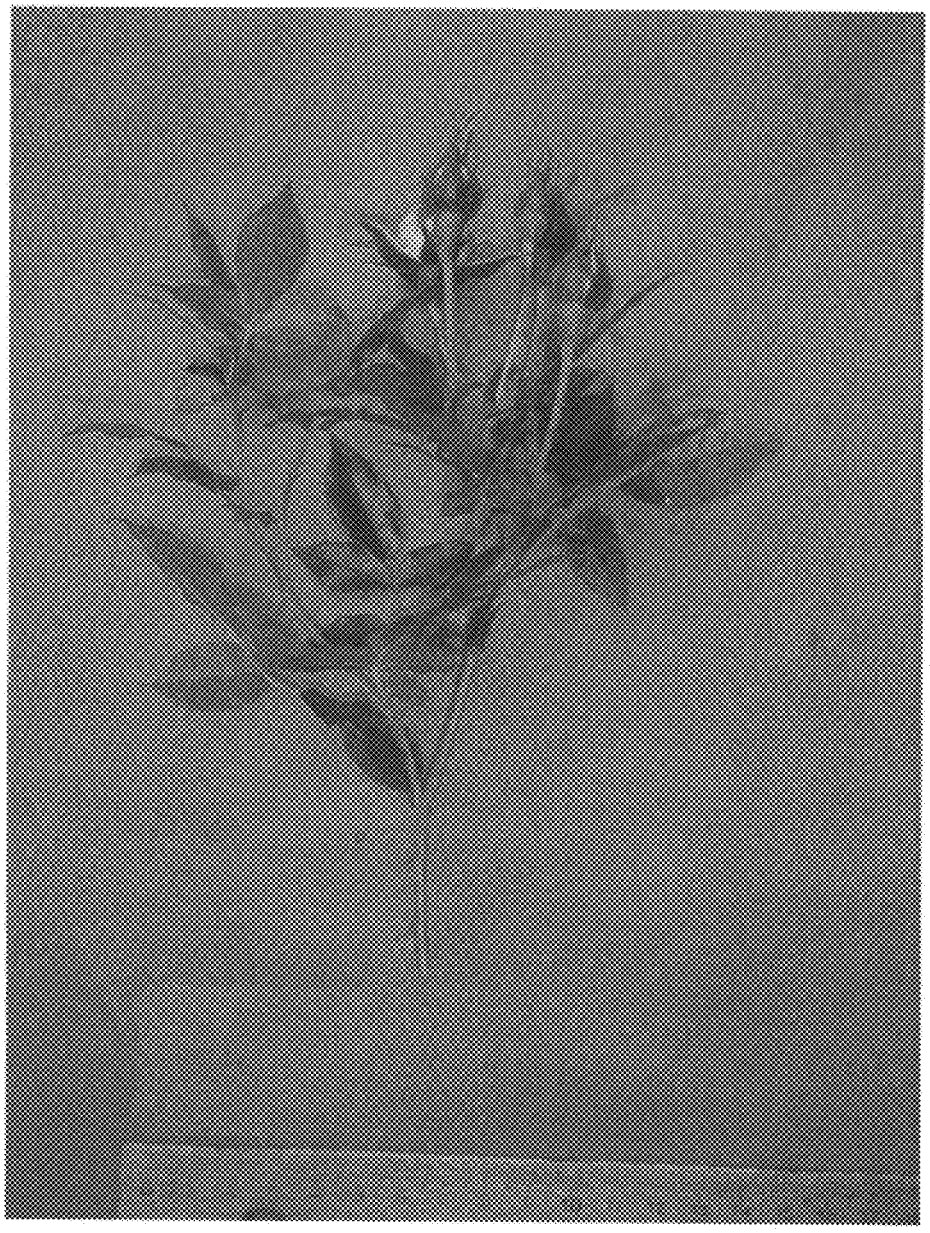
FIG. 3 is a photograph of foliage and buds of the new variety.
Figure 4:
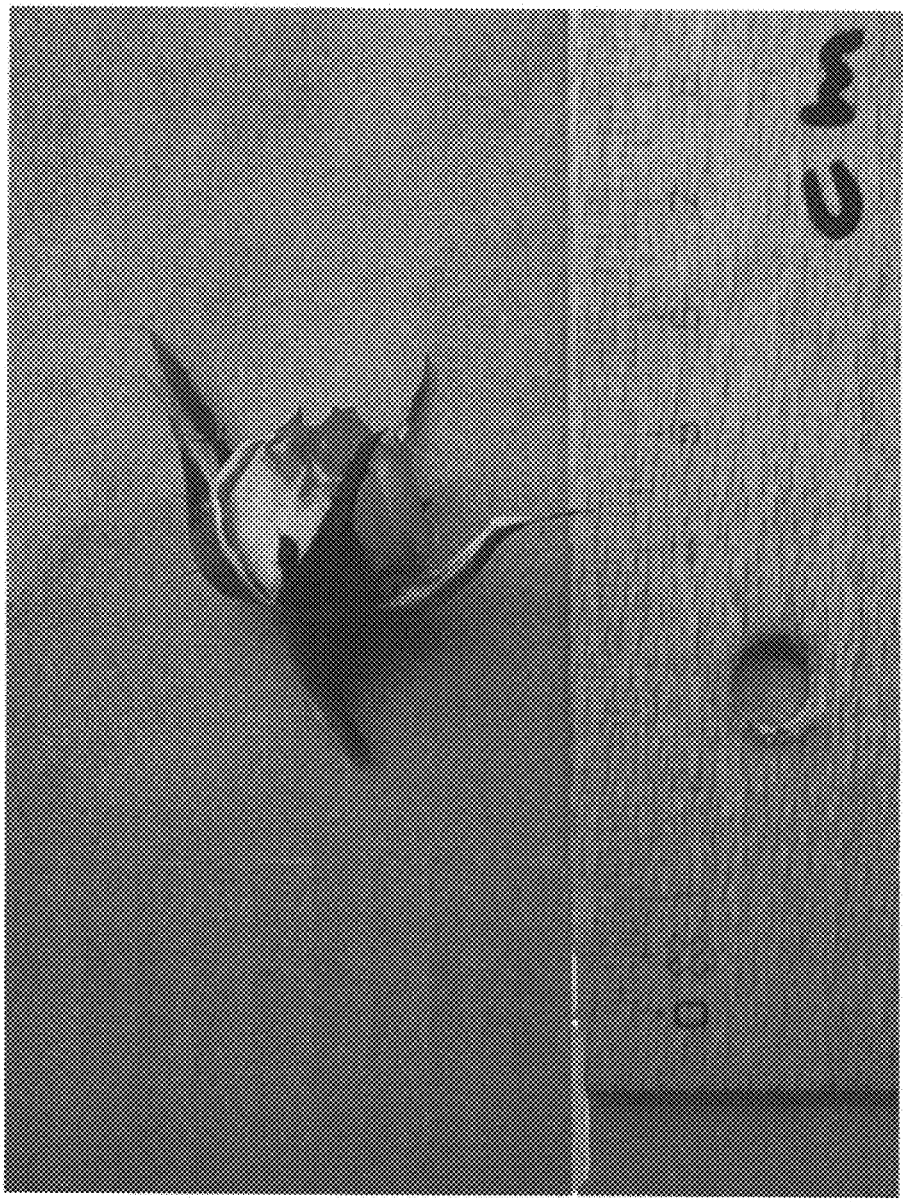
FIG. 4 is a photograph of a partially open bud of the new variety.
Figure 5:
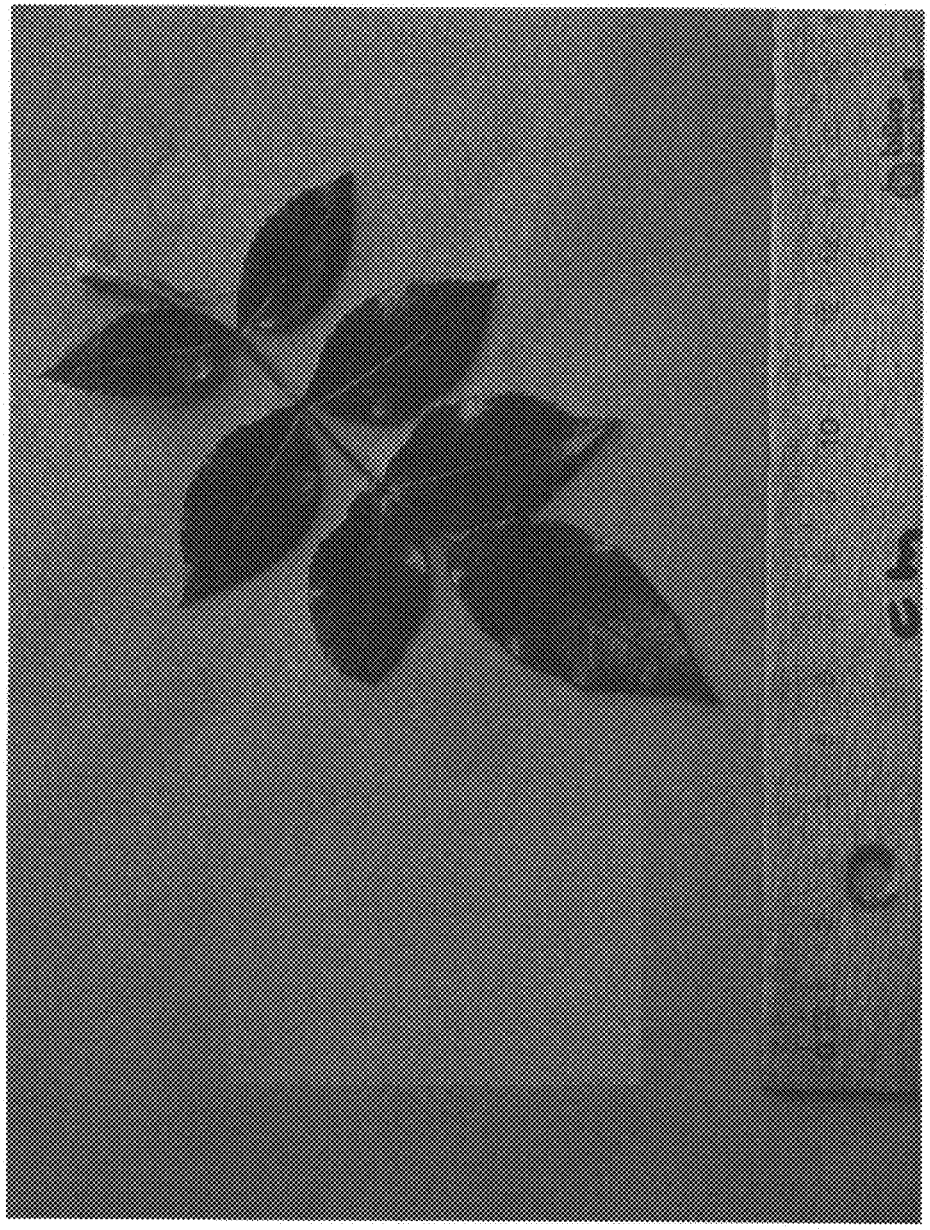
FIG. 5 is a photograph of the adaxial surface of a leaflet of the new variety.
Figure 6:
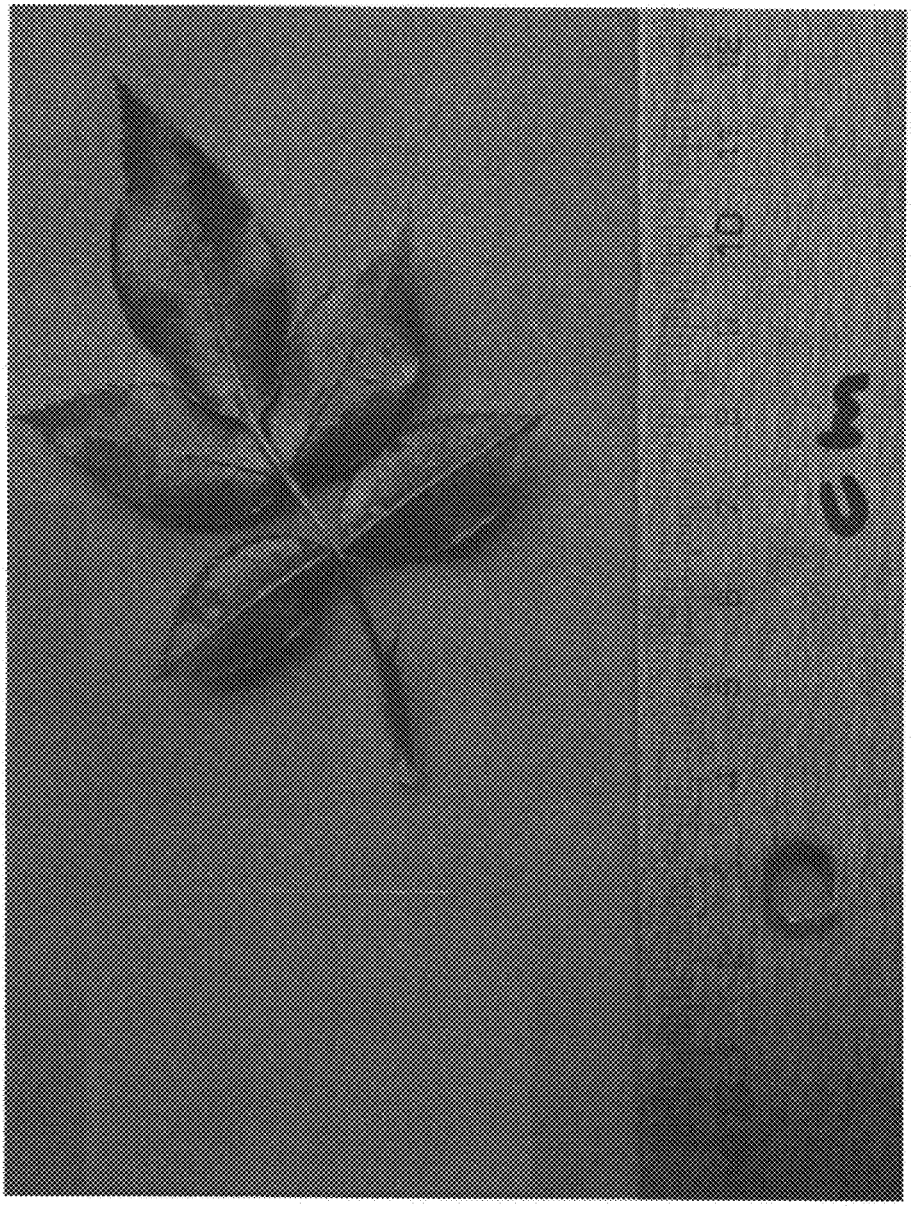
FIG. 6 is a photograph of the abaxial surface of a leaflet of the new variety.
Figure 7:
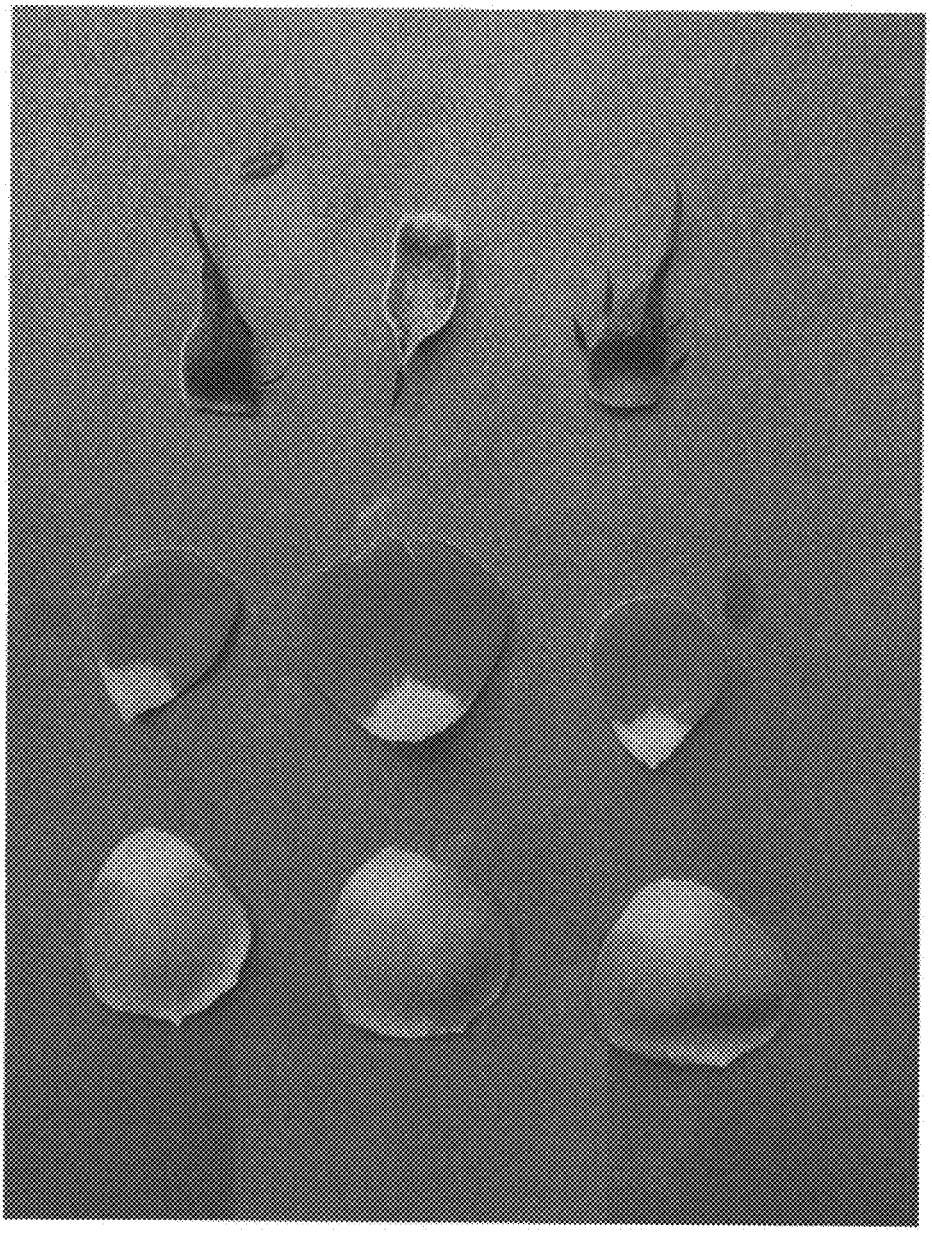
FIG. 7 is a photograph of flower petals and sepals from the new variety.

The following is a detailed description of my new rose cultivar with color descriptions using terminology in accordance with The Royal Horticultural Society (London) Colour Chart (1966), except where ordinary dictionary significance of color is indicated. Observations made from two year old plants being grown outdoors in a garden environment at Uetersen, Germany.

Parentage:

*Seed parent*.—'Top Marks'.

*Pollen parent*.—'Gebrüder Grimm'.

FLOWER

Blooming habit: Continuous.

Bud:

*Size*.—About 1.2 cm long and 1.5 cm in diameter when the petals start to unfurl.

*Form*.—The bud form is short, globular.

*Color*.—When sepals first divide, bud color is Red RHS 50A. When half blown, the upper sides of the petals are Red RHS 50A; and the lower sides of the petals are Yellow RHS 4B.

*Sepals*.—Color: Upper surface: Green RHS 137B. Lower surface: Green RHS 137B. Length: 2.3 cm. Width: 0.7 cm. Shape: Lanceolate. Surface texture: Smooth. There are three lightly appendaged sepals.

*Receptacle*.—Color: Green RHS 141D. Shape: Funnel. Size: Small, about 5 mm long×5 mm wide. Surface: Smooth.

*Peduncle*.—Length: Medium, averaging about 2.8 cm. Surface: Prickly. Color: Green RHS 141D. Strength: Erect.

Bloom:

*Size*.—Medium. Average open diameter is about 5 to 6 cm.

*Borne*.—Many double blooms, many umbels.

*Stems*.—Strength: Normal. Average length is about 40 cm with a diameter of 0.5 cm.

*Form*.—When first open: Bloom is flat. Permanence: Outer petal edges curl slightly.

*Petalage*.—Number of petals under normal conditions: 60-64.

*Color*.—The upper sides of the petals are Red RHS 50A. The reverse sides of the petals are Red RHS 36B. The base of the petals are Yellow RHS 8B. The major color on the upper side is Red RHS 50A. When the flower opens the color turns to a more and more purple red.

*Discoloration*.—The general tonality at the end of the first day: Red RHS 50A. At the end of the third day: Red RHS 50A. Color changing with further aging: Fading to Red-Purple RHS 58C.

*Fragrance*.—None.

Petals:

*Thickness*.—Thin.

*Shape*.—Large petals are oval.

*Surface*.—Smooth.

*Margin*.—Smooth. Apex Shape: Obovate. Base Shape: Rounded.

*Form*.—Flat, tips slightly recurved.

*Arrangement*.—Regular.

*Petaloids*.—Number: 1. Color: Red-Purple RHS 65B.

*Persistence*.—Petals drop off cleanly before drying out.

*Lastingness*.—On the plant: Long, about 20 days. As a cut flower: Not tested.

Reproductive parts:

*Stamens*.—Number: 32. Length: 0.5 cm. Anthers: Length: 0.1 cm. Color: Light Green RHS 145C. Arrangement: Regular around styles. Filaments: Color: Light Green RHS 145D. Length: 0.4 cm. Pollen: Color: Orange RHS 24C.

*Pistils*.—Number: 16. Length: 0.3 cm. Styles: Color: Orange RHS 24D. Length: 0.25 cm. Stigmas: Color: Yellow RHS 11C. Length: 0.05 cm.

*Hips*.—Color: Orange RHS 24D. Size: Medium, 0.7 cm. Shape: Round.

PLANT

*Form*.—Climbing.

*Growth*.—Medium.

*Age at maturity*.—4 years.

*Mature plant*.—Height: Typical — 150 cm to 200 cm. Width: Typical — 50 cm.

*Rootstock*.—Propagated by cuttings.

Foliage: Number of leaflets on normal mid-stem leaves: 5.

*Size*.—Small, about 7.8 cm long×4.6 cm wide.

*Quantity*.—Abundant.

*Color*.—New foliage: Upper side: Green RHS 143A. Lower side: Green RHS 143A. Old foliage: Upper side: Green RHS 137B. Lower side: Green RHS 137C.

Leaflets:

*Size*.—About 2.6 cm long×1.4 cm wide.

*Shape*.—Pointed oval.

*Base shape*.—Rounded.

*Apex shape*.—Pointed.

*Texture*.—Leathery.

*Edge*.—Serrated.

*Serrations*.—Single.

*Petiole*.—Color: Green RHS 138B.

*Petiole rachis*.—Color: Red RHS 36C. Underside: Rough.

*Auricle shape*.—Slender.

*Stipules*.—Length: 1.3 cm, serrated.

*Disease resistance*.—Under normal growing conditions: Mildew: Resistant. Blackspot: Resistant. Rust: Resistant.

*Pest resistance*.—Average.

*Vein color*.—Yellow-Green RHS 145C.

*Venation pattern*.—Pyramidal.

Wood:

*New wood*.—Color: Green RHS 146D. Bark: Smooth.

*Old wood*.—Color: Greyed-Orange RHS 165A. Bark: Rough.

Prickles:

*Quantity*.—On main canes from base: Ordinary, 28 per 32 cm. On laterals from main canes: Ordinary.

*Form*.—Hooked downward.

*Length*.—0.6 cm.

*Color when young*.—Greyed-Orange RHS 166B.

*Color when mature*.—Red RHS 47A.

Small prickles:

*Quantity*.—On main stalks: Few. On laterals: Few.

*Color*.—Red RHS 47A.

Winter hardiness: Hardy to Zone 7A.

I claim:

1. A new and distinct variety of climbing rose plant, substantially as herein illustrated and described.

* * * * *